United States Patent [19]
Edwards

[11] 3,958,000
[45] May 18, 1976

[54] FUNGICIDAL 2-ARYLTHIO-, 2-ALKYLTHIO- AND 2-HALOALKYLTHIO-1,2,4-OXADIAZOLIDINE-3,5-DIONES

[75] Inventor: Laroy H. Edwards, Napa, Calif.

[73] Assignee: Chevron Research Company, San Francisco, Calif.

[22] Filed: Jan. 17, 1975

[21] Appl. No.: 541,915

[52] U.S. Cl. .............................. 424/272; 260/307 B; 260/553 R; 260/553 A
[51] Int. Cl.² ...................................... C07D 271/06
[58] Field of Search ................. 260/307 B; 424/272

[56] References Cited
UNITED STATES PATENTS
3,696,115  10/1972  Zschocke et al. ................ 260/307 B

*Primary Examiner*—Raymond V. Rush
*Attorney, Agent, or Firm*—George F. Magdeburger; Dix A. Newell; Raymond Owyang

[57] ABSTRACT

2-Alkylthio- and 2-alkylthio-4-substituted-1,2,4-oxadiazolidine-3,5-diones, which have fungicidal activity, are prepared by reacting an alkyl or haloalkyl sulfenyl chloride with the alkali metal salt of a 4-substituted-1,2,4-oxadiazolidine-3,5-dione.

11 Claims, No Drawings

FUNGICIDAL 2-ARYLTHIO-, 2-ALKYLTHIO- AND 2-HALOALKYLTHIO-1,2,4-OXADIAZOLIDINE-3,5-DIONES

DESCRIPTION OF THE PRIOR ART

G. Zinner et al, Arch. Pharm. 298, 580 (1965) [Chem. Abst. 64, 11201f (1966)] disclose 4-substituted and 2,4-disubstituted-1,2,4-oxadiazolidine-3,5-diones.

U.S. Pat. No. 3,437,664; U.S. Pat. No. 3,632,599; U.S. Pat. No. 3,696,115; Chem. Abst. 63, 600c (1965); Chem. Abst. 69, 96735s (1968); and Chem. Abst. 76, 153677v (1972) disclose 2,4-disubstituted-1,2,4-oxadiazolidine-3,5-diones.

DESCRIPTION OF THE INVENTION

The 1,2,4-oxadiazolidine-3,5-diones of the invention are represented by Formula (I):

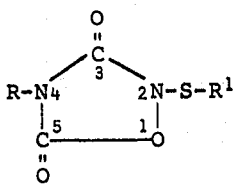

(I)

wherein R is alkyl of 1 to 6 carbon atoms, cycloalkyl of 3 to 8 carbon atoms, preferably of 5 to 6 carbon atoms, phenyl substituted with up to 3 (0 to 3) of the same or different substituents selected from fluoro, chloro, bromo, alkyl of 1 to 4 carbon atoms, alkoxy of 1 to 3 carbon atoms or nitro and $R^1$ is alkyl of 1 to 6 carbon atoms, haloalkyl of 1 to 2 carbon atoms and 1 to 5 of the same or different halogens selected from fluoro, chloro or bromo, or phenyl substituted with up to 2 (0 to 2) of the same or different substituents selected from fluoro, chloro, bromo or alkyl of 1 to 4 carbon atoms.

Representative alkyl groups which R and $R^1$ may represent are methyl, ethyl, propyl, isobutyl, n-pentyl and hexyl.

Representative cycloalkyl groups which R may represent are cyclopropyl, cyclobutyl, cyclopentyl, cyclohexyl, and cyclooctyl.

Representative substituted phenyl groups which R may represent are halophenyls such as o-fluorophenyl, p-fluorophenyl, o-chlorophenyl, p-chlorophenyl, m-bromophenyl, 3,4-dichlorophenyl, 3-chloro-4-bromophenyl and 2,4,6-trichlorophenyl; alkylphenyl such as p-tolyl, 2,4-dimethylphenyl, 3,5-diethylphenyl, 4-isopropylphenyl; haloalkylphenyl such as 2-methyl-4-chlorophenyl and 2-bromo-4-ethylphenyl; alkoxyphenyl such as 2-methoxyphenyl, 4-ethoxyphenyl and 2,4-dipropoxyphenyl; nitrophenyls such as o-nitrophenyl and 2,4-dinitrophenyl; phenyl substituted with different substituents such as 2-nitro-4-chlorophenyl, 2-methyl-4-nitrophenyl, 3-methoxy-4methylphenyl and 2,6-dimethyl-4-methoxyphenyl.

Representative substituted phenyl groups which $R^1$ may represent are m-fuorophenyl, p-chlorophenyl, 3,4-dichlorophenyl, 2,4-dibromophenyl, p-tolyl, and 3,5-dimethylphenyl.

Representative haloalkyl $R^1$ groups are chloromethyl, difluoromethyl, dichloromethyl, dibromomethyl, dichlorofluoro-methyl, trifluoromethyl, tribromomethyl, 1,2,2,2-tetrafluoro-ethyl, 2,2,2-trichloroethyl, 1,2,2,2-tetrachloroethyl, 1-bromo-2,2,2-trichloroethyl, and pentachloroethyl.

Preferably R is alkyl of 1 to 6 carbon atoms, cycloalkyl of 5 to 6 carbon atoms or phenyl substituted with up to 2 (0 to 2) of the same or different substituents defined above. More preferably R is alkyl of 1 to 6 carbon atoms, cycloakyl of 5 to 6 carbon atoms, phenyl or phenyl substituted with 1 to 2 of the same substituents selected from fluoro, chloro, bromo or alkyl of 1 to 4 carbon atoms.

Preferably $R^1$ is alkyl of 1 to 6 carbon atoms, haloalkyl of 2to 5 of the same halogens selected from chloro or bromo, phenyl or phenyl substituted with 1 to 2 of the same halogens selected from fluoro, chloro or bromo. More preferably $R^1$ is polyhaloalkyl of halogens selected from chloro or bromo, especially trichloromethyl or tetrachloroethyl.

Representative compounds of the invention include
2-methylthio-4-methyl-1,2,4-oxadiazolidine-3,5-dione,
2-n-butylthio-4-p-methoxyphenyl-1,2,4-oxadiazolidine-3,5-dione,
2-hexylthio-4-cyclopentyl-1,2,4-oxadiazolidine-3,5-dione,
2-difluorochloromethyl-4-n-butyl-1,2,4-oxadiazolidine-3,5-dione,
2-chloromethyl-4-p-tolyl-1,2,4-oxadiazolidine-3,5-dione,
2-tribromomethyl-4-n-propyl-1,2,4-oxadiazolidine-3,5-dione,
1,1,1,2-tetrachloroethyl-4-p-chlorophenyl-1,2,4-oxadiazolidine -3,5-dione,
1,1,2,2,-tetrabromoethyl-4-o-fluorophenyl-1,2,4-oxadiazolidine-3,5-dione,
1,1,1-tribromo-2-chloroethyl-4-ethyl-1,2,4-oxadiazolidine-3,5-dione,
2-pentachloroethyl-4-methyl-1,2,4-oxadiazolidine-3,5-dione,
2-phenylthio-4-p-nitrophenyl-1,2,4-oxadiazolidine-3,5-dione,
2-p-chlorophenylthio-4-cyclohexyl-1,2,4-oxadiazolidine-3,5-dione, and
2-p-tolylthio-2,4-dichlorophenyl-1,2,4-oxadiazolidine-3,5-dione.

The compounds of the invention are prepared by reacting a hydroxy urea (I) with an alkyl chloroformate (II) and an alkali metal hydroxide (III) to produce an alkali metal salt of a 1,2,4-oxadiazolidine-3,5-dione (IV) and subsequently reacting the alkali metal salt (IV) with a sulfenyl chloride (V) as depicted in Reactions (1) and (2):

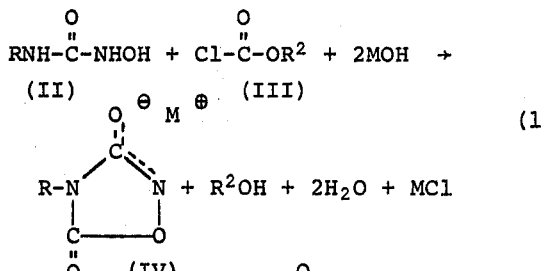

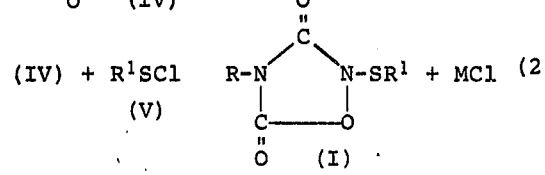

wherein R and R¹ have the same significance as previously defined, R² is lower alkyl, M is an alkali metal, e.g., lithium, sodium and potassium and the dotted line designation represents the electronic delocalization among the illustrated contiguous C, N and O atoms. It is appreciated, of course, that the salt (IV) may also be represented by the following formulas:

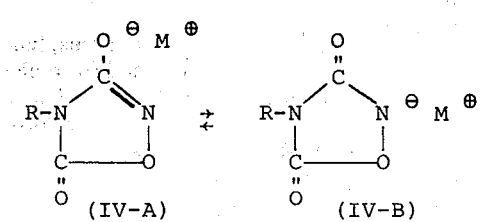

Reaction (1) is conducted by reacting the hydroxy urea (II) with substantially equimolar amounts of the alkyl chloroformate (III) and the alkali metal hydroxide in an inert diluent at a temperature of 25° to 100°C, and subsequently treating the resulting product mixture with an additional equimolar amount of alkali metal hydroxide. Suitable inert diluents for the reaction of the urea and chloroformate include water, cyclic ethers such as tetrahydrofuran, dioxane and diexolane; alkyl aryl ethers such as anisole and phenyl butyl ether; dialkyl ethers such as diethyl ether and dibutyl ether; lower alkyl ethers of polyhydric alcohols or polyoxyalkylene glycols such as ethylene glycol dimethyl ether ad glycol triethyl ether, and alkanols such as methanol and ethanol. Preferably the inert diluent comprises a mixture of water and an organic co-diluent. The salt (IV) is isolated by conventional procedures such as filtration, extraction, crystallization, etc.

Reaction (2) is conducted by reacting the salt (IV) with substantially equimolar amounts of the sulfenyl chloride (V) in an inert diluent at a temperature of 25° to 100°C. Suitable inert diluents include chlorinated alkanes such as methylene chlorine and aromatic hydrocarbons such as toluene and xylene. The 1,2,4-oxadiazoline-3,5-dione product (I) is isolated by conventional procedures such as extraction, filtration, crystallization, drying and chromatography.

The 1,2,4-oxadiazolidine-3,5-diones of the invention are useful for controlling fungi, particularly plant fungal infections caused by controlling fungi, particularly plant fungal infections caused by *Botrytis cinerea*, tomato blights caused by organisms such as *Alternaria solani conidia* and *Phytophthora infestans conidia*, powdery mildew caused by organisms such as *Erysiphe polygoni* and *E. chicoraciarum*, and other fungal infections caused by organisms such as *Pythrium ultimum, Helminthosporum sativum, Fusarium moniliforme, Rhizoctonia solani, Monolinia fructicola* and *Uromyces phaseoli typica*. However, some fungicidal compounds of the invention may be more fungicidally active than others against particular fungi.

When used as fungicides, the compounds of the invention are applied in fungicidally effective amounts to fungi and/or their habitats, such as vegetative hosts and non-vegetative hosts, e.g., animal and industrial products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of applicaton may affect the activity of the fungicide. Thus, the fungicides of the invention may be formulated and applied as granules, as powdery dusts, as wettable powders, as emulsifiable concentrates, as solutions, or any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents, and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier, such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of these techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

Example 1

Preparation of 2-trichloromethylthio-4-cyclohexyl-1,2,4-oxidiazolidine-3,5-dione.

Cyclohexyl isocyanate (50 g, 0.4 mol) in 100 ml dioxane was added dropwise to a solution of 28 g (0.4 mol) hydroxylamine hydrochloride in 40 ml of water and 80 ml of aqueous 22% wt. sodium hydroxide. After, the additiion was completed, the reaction mixture was diluted with 160 ml ethanol and stirred for 30 minutes.

Ethyl chloroformate (47.6 g, 0.44 mol) was added dropwise at about 25°C to the reaction mixture of N-cyclohexyl-N'-hydroxy urea (prepared above) and 88 ml of 22% aqueous sodium hydroxide. After the addition was completed, the reaction mixture was evaporated under reduced pressure. The residue was diluted with methylene chloride, washed with water, dried over magnesium sulfate and evaporated under reduced pressure to give the crude product mixture (predominantly N-carbethoxycarbonyloxy-N-cyclohexyl urea). The product mixture and 29 g (0.42 mol) sodium hydroxide were then dissolved in 500 ml methanol and the resulting solution was stirred for 3 hours at about 25°C. The oxadiazolidinedione sodium salt precipitated [Formula IV, R=cyclohexyl M=sodium]. The salt was separated by filtration and dried. The yield of the salt was 53.5 g.

Trichloromethylsulfenyl chloride [9.3 g, 0.05 mol] was added dropwise to a solution of 10.7 g (0.05 mol) of the oxadiazoledinedione salt in 300 ml methylene chloride. After the addition was completed, the reaction mixture was heated under reflux for 45 minutes. The reaction mixture was then cooled, filtered, washed with water, dried over magnesium sulfate and evaporated under reduced pressure to give the 2-trichloromethylthio-4-cyclohexyl-1,2,4-oxadiazolidine-3,5-dione product, as a solid melting at 103-105°C. The elemental analysis for the product is tabulzed in Table I under Compound No. 1.

The other compounds tabulated in Table I were prepared by a procedure similar to that of this example.

EXAMPLE 2

Fungal spore control

The compounds of the invention were tested for effectiveness against spores by means of a variation of "The Standard Spore Slide-Germination Method for Determining Fungicidal Activity," described in "American Phytopathological Society Journal," Vol. 33, pp 627–632 (1943). The method is designed to measure the fungitoxic activity of fungicidal chemicals, their activity being expressed in terms of percent inhibition of germination of fungus spores. Each compound toxicant to be tested was dissolved in acetone to a concentration of 100 ppm. These solutions were then pipetted into the wells of depression slides and allowed to dry. The wells were filled with a spore suspension of the specified test organsim. The spores were the incubated a in a moist chamber overnight. A group of 100 spores were examined and the number of spores germinated and not germinated was counted and recorded to show the biological activity in terms of the percent germination inhibition. Table II reports the results of this testing.

TABLE I

Compounds of the formula

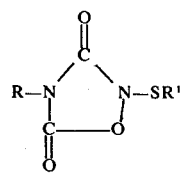

| Compound No. | R | R' | Melting Point, °C. | Elemental Analysis %S Calc. | Found | %Cl Calc. | Found |
|---|---|---|---|---|---|---|---|
| 1 | Cyclohexyl | —CCl$_3$ | 103–105 | 9.6 | 9.5 | 31.9 | 31.0 |
| 2 | Cyclohexyl | —CCl$_2$CCl$_2$H | oil | 8.4 | 8.4 | 37.0 | 36.1 |
| 3 | i-C$_3$H$_7$ | —CCl$_3$ | 104–107 | 10.9 | 10.0 | 36.2 | 34.2 |
| 4 | i-C$_3$H$_7$ | —CCl$_2$CCl$_2$H | oil | 9.4 | 9.3 | 41.5 | 42.1 |
| 5 | p-Cl—φ* | —CCl$_3$ | 139–141 | 8.8 | 8.8 | 39.3 | 38.5 |

*φ = phenyl

TABLE II

| Compound No. | Botrytis cinerea | | Alternaria solani | | Monolinia fructicola | |
| --- | --- | --- | --- | --- | --- | --- |
| | Conc. (ppm) | % Control | Conc. (ppm) | % Control | Conc. (ppm) | % Control |
| 1 | 10 | 100 | 4 | 78 | 10 | 100 |
| 2 | 10 | 100 | 10 | 99 | 10 | 100 |
| 3 | 10 | 100 | 4 | 99 | 10 | 100 |
| 4 | 10 | 100 | 10 | 99 | 10 | 10 |

What is claimed is:

1. A compound of the formula

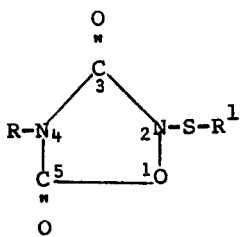

wherein R is alkyl of 1 to 6 carbon atoms, cycloalkyl of 3 to 8 carbon atoms, phenyl substituted with up to 2 of the same or different substituents selected from fluoro, chloro, bromo or alkyl of 1 to 4 carbon atoms, and $R^1$ is haloalkyl of 1 to 2 carbon atoms and of 1 to 5 of the same or different halogens selected from fluoro, chloro or bromo.

2. The compound of claim 1 wherein $R^1$ is trichloromethyl or tetrachloroethyl.

3. The compound of claim 1 wherein R is alkyl of 1 to 6 carbon atoms.

4. The compound of claim 1 wherein R is cycloalkyl of 5 to 6 carbon atoms.

5. The compound of claim 1 wherein R is phenyl substituted with up to 2 of the same or different substituents selected from fluoro, chloro, bromo or alkyl of 1 to 4 carbon atoms.

6. The compound of claim 1 wherein R is alkyl of 1 to 6 carbon atoms, cycloalkyl of 5 to 6 carbon atoms or phenyl substituted with up to 2 of the same substituent selected from fluoro, chloro, bromo or alkyl of 1 to 4 carbon atoms and $R^1$ is haloalkyl of 1 to 2 carbon atoms and 2 to 5 of the same halogens selected from chloro or bromo.

7. The compound of claim 1 wherein R is isopropyl and $R^1$ is trichloromethyl.

8. A fungicidal composition comprising a fungicidally effective amount of the compound of claim 1 and a biologically inert carrier.

9. A method for controlling fungi which comprises applying to said fungi or their habitat a fungicidally effective amount of the compound of claim 1.

10. The composition of claim 8 wherein R is alkyl of 1 to 6 carbon atoms, cycloalkyl of 5 to 6 carbon atoms or phenyl substituted with up to 2 of the same substituents selected from fluoro, chloro, bromo or alkyl of 1 to 4 carbon atoms and $R^1$ is haloalkyl of 1 to 2 carbon atoms and 2 to 5 of the same halogens selected from chloro or bromo.

11. The method of claim 9 wherein R is alkyl of 1 to 6 carbon atoms, cycloalkyl of 5 to 6 carbon atoms or phenyl substituted with up to 2 of the same substituents selected from fluoro, chloro, bromo or alkyl of 1 to 4 carbon atoms and $R^1$ is haloalkyl of 1 to 2 carbon atoms and 2 to 5 of the same halogens selected from chloro or bromo.

* * * * *